US 11,058,490 B2

United States Patent
Varghese et al.

(10) Patent No.: US 11,058,490 B2
(45) Date of Patent: Jul. 13, 2021

(54) LIGHT BASED SKIN TREATMENT DEVICE

(71) Applicant: KONINKLIJKE PHILIPS N.V., Eindhoven (NL)

(72) Inventors: Babu Varghese, Eindhoven (NL); Rieko Verhagen, Vught (NL)

(73) Assignee: Koninklijke Philips N.V., Eindhoven (NL)

( * ) Notice: Subject to any disclaimer, the term of this patent is extended or adjusted under 35 U.S.C. 154(b) by 102 days.

(21) Appl. No.: 16/324,350

(22) PCT Filed: Aug. 8, 2017

(86) PCT No.: PCT/EP2017/070077
§ 371 (c)(1),
(2) Date: Feb. 8, 2019

(87) PCT Pub. No.: WO2018/029196
PCT Pub. Date: Feb. 15, 2018

(65) Prior Publication Data
US 2019/0183574 A1 Jun. 20, 2019

(30) Foreign Application Priority Data

Aug. 9, 2016 (EP) .................................... 16183299
Aug. 9, 2016 (EP) .................................... 16183301
(Continued)

(51) Int. Cl.
*A61B 18/20* (2006.01)
*A61B 18/00* (2006.01)

(52) U.S. Cl.
CPC .... *A61B 18/203* (2013.01); *A61B 2018/0047* (2013.01); *A61B 2018/00107* (2013.01);
(Continued)

(58) Field of Classification Search
CPC ........ A61B 18/203; A61B 2018/00107; A61B 2018/00452; A61B 2018/0047;
(Continued)

(56) References Cited

U.S. PATENT DOCUMENTS

| 2003/0074150 A1 | 4/2003 | Goldstein |
| 2005/0078383 A1* | 4/2005 | Jones .................. G02B 6/4206 359/717 |

(Continued)

FOREIGN PATENT DOCUMENTS

| EP | 2548617 A2 | 12/2013 |
| WO | WO2008001284 A2 | 1/2008 |

OTHER PUBLICATIONS

Habbema, L. et al., "Efficacy of Minimally Invasive Nonthermal Laser-Induced Optical Breakdown Technology for Skin Rejuvenation", Lasers in Medical Science 28 (3), pp. 935-940, 2013.
Habbema, L. et al., "Minimally Invasive Non-Thermal Laser Technology Using Laser-Induced Optical Breakdown for Skin Rejuvenation," Journal of Biophotonics 5 (2), pp. 194-199, 2012.

*Primary Examiner* — Jonathan T Kuo

(57) ABSTRACT

A light based skin treatment device comprises a laser light source for providing a pulsed incident light beam for treating skin by laser induced optical breakdown of hair or skin tissue. In one arrangement, a focusing system has a pre-focusing lens for increasing the convergence of the an incident light beam and a skin contact lens having convex light input and light exit surfaces. The focal spot position is controlled by adjusting a spacing between the pre-focusing lens and the skin contact lens. In another arrangement, there is an adjustable lens system before an adjustable focusing system for providing compensation for aberration in the adjustable focusing system.

20 Claims, 4 Drawing Sheets

(30) Foreign Application Priority Data

Dec. 28, 2016 (EP) .................................... 16207164
Dec. 30, 2016 (EP) .................................... 16207590

(52) U.S. Cl.
CPC .............. *A61B 2018/00452* (2013.01); *A61B 2018/00476* (2013.01); *A61B 2018/202* (2013.01); *A61B 2018/20355* (2017.05); *A61B 2018/20359* (2017.05); *A61B 2018/20361* (2017.05); *A61B 2018/20553* (2017.05)

(58) Field of Classification Search
CPC .... A61B 2018/00476; A61B 2018/202; A61B 2018/20355; A61B 2018/20359; A61B 2018/20361; A61B 2018/20553; A61B 18/20–18/28; A61N 5/06–2005/073
See application file for complete search history.

(56) References Cited

U.S. PATENT DOCUMENTS

| | | | |
|---|---|---|---|
| 2007/0121213 A1 | 5/2007 | Tseng | |
| 2008/0132886 A1 | 6/2008 | Cohen | |
| 2008/0228178 A1 | 9/2008 | Robbert | |
| 2008/0231966 A1 | 9/2008 | Hendriks | |
| 2008/0279070 A1* | 11/2008 | Zijp | G11B 7/1374 369/53.17 |
| 2011/0118713 A1* | 5/2011 | Raksi | A61F 9/00814 606/6 |
| 2015/0051593 A1* | 2/2015 | Johnson | A61N 5/0617 606/9 |
| 2015/0328480 A1* | 11/2015 | Wang | A61N 5/0619 607/89 |

* cited by examiner

LIGHT BASED SKIN TREATMENT DEVICE

FIELD OF THE INVENTION

This invention relates to device for generating laser induced optical breakdown in skin tissue and as such can be used for (cosmetic) treatment of skin of humans or animals. The device comprises a light source and an optical system for focusing the incident light beam of the light source in a focal spot located outside the device.

BACKGROUND OF THE INVENTION

Such light based skin treatment devices are, e.g., used for cosmetic treatment such as e.g. wrinkle treatment and for hair cutting. In light based wrinkle treatment, the device creates a focal spot in a dermis layer of the skin to be treated. The power and pulse duration of the laser and the dimension of the focal spot are selected such that a laser induced optical breakdown (LIOB) phenomenon affects the skin in order to stimulate re-growth of skin tissue and, therewith, to reduce wrinkles. An example of such device is disclosed in the international patent application published as WO2008/001284.

In light based hair cutting, the incident light beam is focused inside the hair and the LIOB phenomenon causes the hair to be cut through. For example, the international patent application published as WO2005/011510 describes a device for shortening hairs comprising a laser source for generating a laser beam during a predetermined pulse time, an optical system for focusing the laser beam into a focal spot and a laser beam manipulator for positioning the focal spot in a target position. A dimension of the focal spot and a power of the generated laser beam are such that in the focal spot the laser beam has a power density which is above a characteristic threshold value for hair tissue above which, for the predetermine pulse time, a laser induced optical breakdown (LIOB) phenomenon occurs in the hair tissue.

In general, laser induced optical breakdown (LIOB) occurs in media, which are transparent or semi-transparent for the wavelength of the laser beam, when the power density ($W/cm^2$) of the laser beam in the focal spot exceeds a threshold value which is characteristic for the particular medium. Below the threshold value, the particular medium has relatively low linear absorption properties for the particular wavelength of the laser beam. Above the threshold value, the medium has strongly non-linear absorption properties for the particular wavelength of the laser beam, which are the result of ionization of the medium and the formation of plasma. This LIOB phenomenon results in a number of mechanical effects, such as cavitation and the generation of shock waves, which damage the medium in positions surrounding the position of the LIOB phenomenon.

It has been found that the LIOB phenomenon can be used to break and shorten hairs growing from skin. Hair tissue is transparent or semi-transparent for wavelengths between approximately 500 nm and 2000 nm. For each value of the wavelength within this range, LIOB phenomena occur in the hair tissue at the location of the focal spot when the power density ($W/cm^2$) of the laser beam in the focal spot exceeds a threshold value which is characteristic for the hair tissue. Said threshold value is rather close to the threshold value which is characteristic for aqueous media and tissue and is dependent on the pulse time of the laser beam. In particular, the threshold value of the required power density decreases when the pulse time increases.

In order to achieve mechanical effects as a result of the LIOB phenomenon which are sufficiently effective so as to cause significant damage, i.e. at least initial breakage of a hair, a pulse time in the order of, for example, 10 ns suffices. For this value of the pulse time, the threshold value of the power density of the laser beam in the focal spot is in the order of $2*10^{10}$ $W/cm^2$. For the described pulse time and with a sufficiently small dimension of the focal spot obtained, for example, by means of a lens having a sufficiently large numerical aperture, this threshold value can be achieved with a total pulse energy of only a few tenths of a millijoule. Parameter values of similar order can be used to generate the LIOB effect in skin tissue as described in WO2008/001284 in more detail.

SUMMARY OF THE INVENTION

A problem which can arise is that parts of the optical system through which the light exits the device (light exit window) can be damaged by the products of the LIOB (shock wave, plasma, high power density). A damaged light exit part has a detrimental effect on the ability of the device to provide a sufficiently tight focus at the desired position, which may reduce the efficacy of the treatment process and/or may increase the occurrence of adverse side effects, such as skin irritation.

There is therefore a need for a LIOB generation device in which coupling of light into the skin is ensured without damage to the light exit window.

A professional LIOB based skin treatment device is required to create lesions at different or multiple depths inside the skin to obtain higher treatment efficacy and/or, in particular, for the treatment of deep wrinkles, tattoos, or other skin characteristics. Also, skin is not evenly thick across a human's skin area. The range of depth of such a device is for example preferably in the range of 100 µm-1000 µm. Furthermore, the device should be able to provide this variable depth focus feature without excessively complicated system modifications. Ideally, the treatment depth should be adjustable without intervention of a technical specialist. It is also desirable for the device to allow fast treatment at various different treatment depths to suit a number of application areas.

The requirements of users to be able to treat at various depths thus mainly relates to the optimization of treatment efficacy.

The maximum attainable treatment depth is generally limited by the amount of available laser power and the physical depth of the dermis on the one hand, and by the proximity to the light exit window of the device on the other hand. Treating too close to the window (i.e. the final optical element in the laser path) may lead to optical breakdown in the window, causing permanent failure.

Single lenses incorporating both high numerical aperture and large free working distance are typically relatively bulky. As an example, the weight of typical known water immersion objectives, having typical free working distances in water of 3.3 and 2.2 mm for example, is considerably too high to allow for rapid acceleration during scanning. Additionally, their clear aperture is large, leading to relatively bulky scanning optics required to deflect the beam. A further challenge related to such a general purpose objective lens is that it will not have been optimized for use with focusing inside skin, leading to reduced performance in these kinds of applications.

A further problem which thus arises in a system having an adjustable focal depth is that when the beam is focused at multiple depths inside the skin, the beam quality in the focus will be deteriorated resulting from the (spherical) aberration. These aberrations are introduced by the varying target depth of the different objectives and the variations in skin humidity from area to area of a subject and from subject to subject. The reduction in the quality of the beam in the focus resulting from aberrations prevents the occurrence of LIOB and thereby gives poor efficacy of treatment.

There is therefore a need for a LIOB generation device in which coupling of light into the skin is improved or even ensured for different focal depths within the skin.

It is an object of the invention to at least partly fulfill one or more of the aforementioned needs.

This object is achieved with the invention as defined by the independent claims. The dependent claims provide advantageous embodiments.

Examples in accordance with a first aspect of the invention provide a device comprising:
a light source for providing a pulsed incident light beam for treating skin by laser induced optical breakdown of hair or skin tissue;
a focusing system for focusing the incident light beam into a focal spot in the hair or skin tissue, wherein the focusing system comprises:
   a pre-focusing lens, wherein the incident light beam to the pre-focusing lens is convergent and the pre-focusing lens is for increasing the convergence of the incident light beam; and
   a focusing lens having convex light input surface and a convex skin-contacting light exit surface, wherein the focusing lens has a refractive index in the range 1.4 to 1.6 at the wavelength of the pulsed incident light beam; and
a focus controller for controlling the distance from the focusing system to the focal spot by adjusting a spacing between the pre-focusing lens and the focusing lens.

This device can be for generating LIOB in skin or hair of a human being or animal. The device can be for treatment and in particular cosmetic treatment of skin of such human being or animal. The device can be specifically adapted for this purpose and thus be a light based skin treatment device.

This arrangement provides a focusing system which gives a controllable depth, and which can be implemented with low cost and with simple applicability to the system. This provides an improvement to other solutions which could implement the desired free working distances. For example, commercial aspherical and spherical optics could be used which are typically designed for application in blue-ray players, CD players, DVD players, and at optical telecommunications wavelengths. However such standard spherical optics are typically bulky for ease of handling. These optics also give low performance for focusing into the skin to create LIOB as their optical and material properties are not satisfactory.

The invention enables an improved combination of low weight, large free working distance, and proper skin coupling geometry.

The pre-focusing lens may comprise an aspheric lens. A commercial aspheric lens may for example be used in combination with custom spherical optics. The development of manufacturing techniques for miniature aspheric optics in is still behind the development of custom spherical optics. Most aspheric micro-optics are manufactured using compression molding of low Tg glass materials and involves complicated iterative mold design. Alternative solutions involve molding of plastic optics and molding of liquid sol-gel fused silica.

Although these last two techniques do not involve the complicated high temperature mold design step, they still require some iteration in the process.

Designs incorporating the combination of fully customized spherical and aspherical optics can achieve the highest values for the numerical aperture (NA) such as NA>0.8. For example NA up to 1.2 can be used which is feasible when in contact with a medium such as skin.

The pre-focusing lens may comprise:
a convex light input surface; and
a planar light output surface or a convex light output surface with an average radius of curvature greater than the average radius of curvature of the light input surface.

The focusing lens can have an index of refraction of equal to or between 1.4 and 1.6. to match the refractive index of skin as much as possible to therewith reduce reflections at the lens exit surface. Preferably the lens has an Abbe number of between 50 and 85 to reduce color dispersion. The lens can be made of BK glass such as preferably BK7 glass or be made of fused silica. These types of lenses are preferred in view of being able to withstand the high light intensities used for creating the LIOB effect in skin while having refractive indices close to that of skin.

The outer surface of the focusing lens, the light exit surface, preferably comprises an anti-reflection coating. This can reduce reflections of the laser light used as this is high intensity. This prevents damage to the focusing system itself from reflected light from the skin or the lens surface itself. Such reflection can be particularly significant with the high light intensities used for the LIOB generation in skin.

In one arrangement, the device further comprises an adjustable lens system arranged in the light path before the focusing system for providing compensation for aberration in the focusing system. This enables the LIOB efficiency to be maintained at different focal depths. The adjustment preferably is achieved electrically such as with electrically tunable lenses of which focal distance can be altered electrically.

In a first example, the adjustable lens system comprises an electrically tunable lens such as an electrically tunable polymer material based lens. The adjustable lens system may then further comprise a negative lens at the output of the electrically tunable lens. This negative lens provides compensation for the initial shape of the electrically tunable lens.

In a second example, the adjustable lens system comprises an electrowetting or fluid focus lens.

The device preferably comprises a scanning system, wherein the adjustable lens system is provided at the input to the scanning system.

The invention provides a method comprising:
providing a pulsed incident light beam for generating laser induced optical breakdown of hair or skin tissue;
focusing the incident light beam into a focal spot in the hair or skin tissue by:
   increasing the convergence of the incident light beam using a pre-focusing lens;
   focusing the light exiting the pre-focusing lens into the skin using a focusing lens which is in contact with the skin and having convex light input and light exit surfaces, wherein the focusing lens has a refractive index in the range 1.4 to 1.6 at the wavelength of the pulsed incident light beam; and
   controlling the distance from the focusing system to the focal spot by adjusting a spacing between the pre-focusing lens and the focusing lens.

Examples in accordance with a second aspect of the invention provide a device comprising:

a light source for providing a pulsed incident light beam for generating laser induced optical breakdown of hair or skin tissue;

an adjustable focusing system for focusing the incident light beam into a focal spot in the hair or skin tissue;

a scanning system for scanning the focal spot; and an electrically adjustable lens system arranged in the light path before the adjustable focusing system for providing compensation for aberration in the adjustable focusing system, wherein the adjustable lens system is at the input to the scanning system.

This adjustable lens system enables the LIOB efficiency to be maintained at different focal depths.

The adjustable focusing system may be a focusing system as defined for the first aspect of the invention.

In a first example, the adjustable lens system comprises an electrically tunable polymer lens. The adjustable lens system may then further comprise a negative lens at the output of the electrically tunable polymer lens. This negative lens provides compensation for the initial shape of the polymer lens.

In a second example, the adjustable lens system comprises an electrowetting lens.

The adjustable focusing system preferably comprises:

a pre-focusing lens for increasing the convergence of the incident light beam; and a focusing lens having convex light input and light exit surfaces, and the device further comprises a focus controller for controlling the distance from the focusing system to the focal spot by adjusting a spacing between the pre-focusing lens and the focusing lens.

Thus, the focusing system may then be based on the first aspect described above. All features defined for the first aspect can be used for the second aspect. Thus, as in the first aspect, the pre-focusing lens may comprise an aspheric lens. It may comprise a convex light input surface and a planar light output surface or a convex light output surface with an average radius of curvature greater than the average radius of curvature of the light input surface.

The focusing lens may be formed of BK7 glass or fused silica, and the outer surface of the skin contact lens for contacting the skin preferably comprises an anti-reflection coating.

The second aspect also provides a light based skin treatment method comprising:

providing a pulsed incident light beam for treating skin by laser induced optical breakdown of hair or skin tissue;

focusing the incident light beam into a focal spot in the hair or skin tissue using an adjustable focusing system;

scanning the focal spot across the skin using a scanning system; and providing compensation for aberration in the adjustable focusing system using an electrically adjustable lens system before the adjustable focusing system at the input to the scanning system.

The methods or uses of the device according to the invention are preferably non-therapeutic methods or uses, in particular cosmetic methods, for altering skin appearance such as skin rejuvenation, wrinkle reduction or skin hair removal and the like.

BRIEF DESCRIPTION OF THE DRAWINGS

Examples of the invention will now be described in detail with reference to the accompanying drawings, in which.

DETAILED DESCRIPTION OF THE INVENTION

This invention relates to device for light based treatment of skin. The device comprises a light source and an optical system for focusing the incident light beam of the light source outside in a focal spot located outside the device. The focused light can thus be used for treating skin tissue of an animal or person by laser induced optical breakdown (LIOB) of the skin tissue or a hair therein.

In a first aspect, a focusing system has a pre-focusing lens for increasing the convergence of the incident light beam and a focusing lens having convex light input and light exit surfaces. The focal spot position is controlled by adjusting a spacing between the pre-focusing lens and the focusing lens.

In a second aspect, there is again an adjustable focusing system for focusing the incident light beam into a focal spot in the hair or skin tissue, and there is additionally an adjustable lens system before the adjustable focusing system for providing compensation for aberration in the adjustable focusing system.

For both aspects and others, preferably the focusing lens is adapted for use as a skin contacting lens and as such is a skin contacting lens. Media for improving optical contact between the lens and skin such as refractive index matching fluids may be applied between lens and skin when a device is in use and the lens material or surface material may be adapted to better match the refractive index of the fluid or the skin itself. Alternatively, the focusing lens can also be used in conjunction with an optical window through which the light is focused in the skin. This optical window can be part of the device and as such even be part of the focusing system. Such an example is described in US2015/0051593. The optical window can then be applied to the skin such that the focusing lens can be positioned near the window or even in contact with the window. In another alternative setup an optical window separate from the device is applied to the skin with one of its sides. This separate optical window may thus be an optically transparent sheet (single or multilayer) of relatively small thickness and pliable/bendable/flexible such that it at least partly conforms to skin curvature. An example is disclosed in WO2013/128380. The focusing lens can then be an optically transparent sheet contacting lens contacting lens. A separate window from the focusing lens enables the two to be made of different materials in order to optimize optical contact (e.g. better match of refractive indices) between skin and focusing lens as e.g. described in WO2013/128380.

Before describing the invention in detail, an outline will be given of one example of the type of device to which the invention relates. Other devices for which the invention will work are however conceivable.

Figure 1:
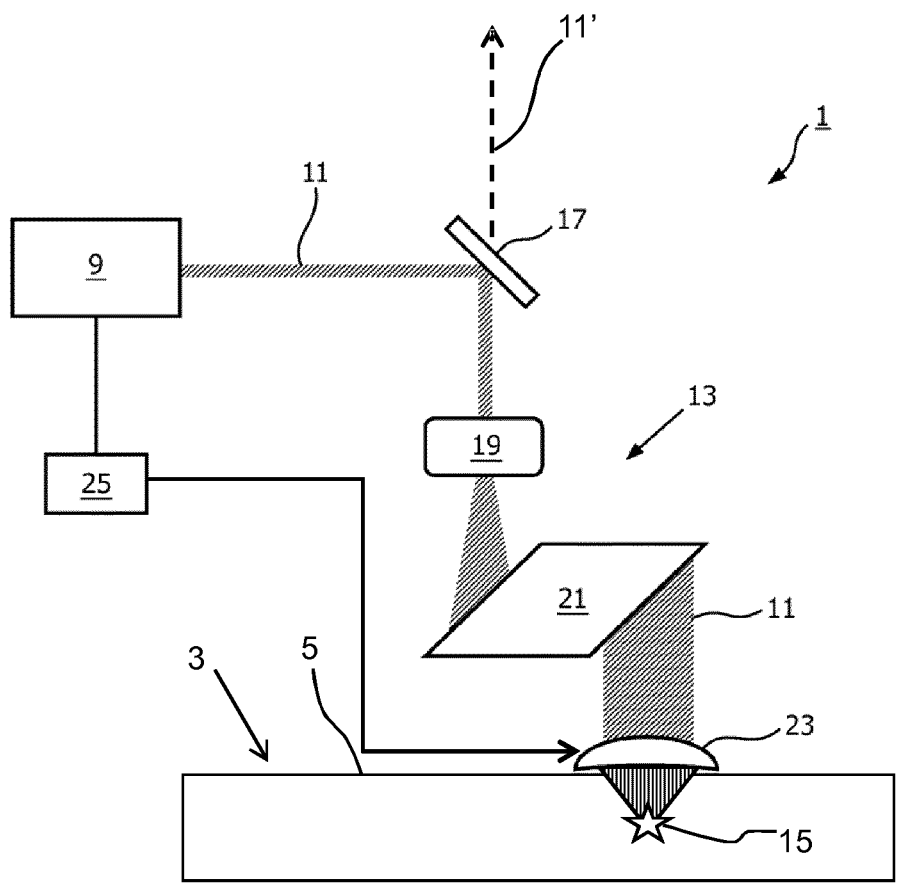
FIG. 1 schematically shows a LIOB skin treatment device.

FIG. 1 shows a LIOB system 1 for treatment of a skin 3 having a surface 5. The surface in this case is bare skin, but could be covered with a transparent sheet for index matching as described herein above.

The system 1 comprises a light source 9 for generating a laser light beam 11 during at least a predetermined pulse time, and it comprises an optical system 13 for focusing the laser beam 11 into a focal spot 15 and for positioning the focal spot 15 in a target position within the skin 3, which is at least partly transparent to the light from the light source 9. In other words, preferably the light source is one providing light that is not substantially or entirely not absorbed by skin tissue.

The example of the optical system 13 schematically indicated in FIG. 1 comprises a beam reflecting system 17, a beam shaping system 19, a beam scanning system 21 and a focusing system 23, which systems may comprise one or more mirrors, prisms, beam splitters, polarizers, optical fibers, lenses, apertures, shutters, etc, that are suitable for manipulating the light of the light source. For example, the scanning system comprises scanning prisms. The beam reflecting system 17 in this case is a dichroic beam splitter. The beam reflecting and beam shaping provide expanding or compressing, and introducing additional convergence or divergence to the light beam.

The focusing system has focusing depth selection, beam shaping and focusing and a light output surface/window which in this case is also suitable for making contact with the skin. Although not specifically drawn in FIG. 1, there may be a contour following suspension system for manipulating the focusing system such that it is able to maintain contact of the light output surface with the skin surface when the device is in use and whether or not the skin is covered by a transparent sheet applied to it.

At least part of the optical system 13 and/or the beam path of the laser beam 11 may be enclosed in light blocking enclosure such as e.g. comprising opaque tubes and/or one or more optical fibers. This can be done for e.g. user (eye)-safety, as light beams can be of high energy in LIOB based devices.

The light source 9 is preferably a laser light source configured to emit a predetermined number of laser pulses at a predetermined wavelength (not appreciably or better not at all, absorbed by skin tissue) and with a predetermined pulse duration and repetition rate or frequency. The system 1 is configurable such that the target position of the focal spot 15 can be beneath the surface of the skin. The dimension of the focal spot 15 and the power of the generated laser beam are such that, in the focal spot 15, the laser beam 11 has a power density, which is above the characteristic threshold value for the skin tissue, above which, for the predetermined pulse time, a laser-induced optical breakdown event occurs.

There may be a light guiding system between the laser source 9 and the beam dichroic beam splitter 17 in the form of an articulating arm (not shown in FIG. 1). The arm can have tubes and mirrors for guiding the light inside them. The beam reflecting system 17 and subsequent components then form part of a handheld piece with appropriate grip for holding by a user. The articulating arm allows easy three dimensional movement of the hand piece during use of the device. Because of alignment errors in the mirrors of the articulating arm, the beam may be expanded before entering the articulating arm and then compressed afterwards before beam steering and aberration correction. Other suitable light guiding structures can also be used. The hand piece can be made detachable from the light guiding structures, allowing easy replacement.

The skin 3 comprises multiple layers with different optical properties. The epidermis is composed of the outermost layers and forms a waterproof protective barrier. The outermost layer of the epidermis is the stratum corneum which, due to its microscopic fluctuations in roughness, impedes the coupling of light between the device 1 and the skin 3. For this reason, a coupling fluid is preferably provided between the focusing system and the skin, with a refractive index which aims to match that of the skin and/or an exit lens of the focusing system.

Underneath the epidermis, the dermis is situated. The dermis comprises the collagen fibers at which the skin treatment with a device according to the invention is aimed.

The purpose of the skin treatment is to create the focus 15 of the light beam 11 in the dermis in order to create microscopic lesions which in turn may result in new collagen formation due to as is believed the normal repair mechanisms operative in the skin to be triggered by the lesions.

The light source 9 is controllable with an optional controller 25, which may provide a user interface for setting e.g. laser intensities, pulse width or duration and repetition rates or even wavelength tuning if possible with the source at hand. Also, one or more parts of the optical system 13 may be controllable with an optional controller (not shown), which may be integrated with the optional light source controller 25 to control one or more properties of the target position and/or the focal spot such as focal spot depth measured as of the light exit surface of the device.

Laser beam focusing parameters may be determined by appropriate settings of a beam shaping and/or focusing system, e.g. by adjustment of the numerical aperture of the focusing system. Suitable values for the numerical aperture NA of the focusing system may be chosen from a range $0.05 < NA < nm$, wherein nm is the index of refraction of the medium for the laser wavelength, during operation. Exemplifying and suitable NA values for various beam energies that can be used with this invention have been discloses in WO2008001284. Also wavelength ranges for laser sources and their energy settings suitable for use with the current invention have been discloses in WO2008001284. Therefore those skilled in the art are referred to WO2008001284 for these and other (detailed) options as well as to methods of operation that can be implemented in or used with a device of the current invention. It is noted that such options and methods of use can be implemented without the described sensor feedback systems and methods of WO2008001284.

One suitable light source comprises a Q-switched Nd:YAG laser emitting laser pulses at a wavelength of about 1064 nm with a pulse duration of about 5-10 ns, although other lasers, e.g. a Nd:Cr:Yag 3-level laser and/or diode lasers may be used as well.

In the example device of FIG. 1, the beam reflecting system 17 comprises a dichroic beam splitter which reflects the laser light but passes visible wavelength light in this case preferably as in this case green light of the double frequency of the laser light source. Thus, received visible wavelength light from the skin 3 is captured by the optical system and is provided as a feedback signal 11' which can be used for controlling the system either manually or automatically. It is known that LIOB can generate frequency doubling of light in the skin under certain circumstances and this may be used to measure or estimate the actual depth of treatment and/or extent of treatment.

Note that the specific scanning and beam movement design outlined above is one example only. As outlined above, the current invention relates to a focusing system design, which can be used in many other different system configurations for generation of LIOB in skin, for example a low repetition rate laser with the lens arrangement of the invention may be used as a stand-alone device without using any scanning such that at least scanning system 21 is not present. In that case for treating larger areas of skin, the consumer or the operator can move the device manually.

The focusing depth provided by the focusing system 23 is preferably adjustable.

Figure 2:
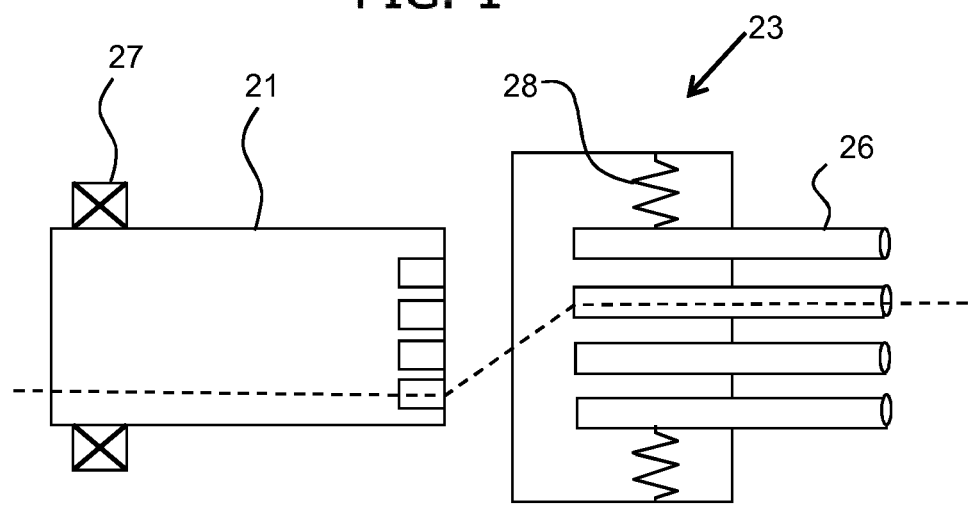
FIG. 2 shows one way to implement focal depth control.

FIG. 2 shows one way to implement such adjustment. The focusing system 23 comprises a set of focusing lenses having a light output surface/windows 26 each with a different focus depth, and an optical path is provided to one of the lenses by the scanner motor 27, which rotates the scanning system 21. The output surfaces/windows 26 are held by a contour following suspension system 28. The output surfaces/windows are thus arranged around a circular path, and a notch system provides positioning with respect to the scanning system 21. There may be four output windows 26, and thus four lens sets each separately spring loaded to provide contour following.

The scanning system 21 is used to scan the focus across an area of skin.

An electromechanical system operates the scanning system to move the beam position and also to move the focusing system 23 (i.e. the objective lens) in synchronism. Thus, the focusing system is physically scanned, whereas all components upstream of the scanning system 21 remain static.

One example of laser that may be used in the system of FIG. 1 has a maximum repetition frequency of 1000 Hz, and a typical treatment regime uses a lesion pitch of 200 μm, resulting in a typical maximum scan speed of 200 mm/s. This scan speed rules out any manual-scanning-only options because of lack of control when applying these scanning speeds by hand.

Additionally, any start-stop scanning system will be severely challenged to reach this scanning speed over a short distance of acceleration, leading to mechanical vibrations and ineffective use of the capacity of the laser. A more easily controlled slower scanning speed will significantly increase the treatment time for large surface areas.

To overcome this challenge a continuous motion scanning may be used, preferably on the basis of rotary motion, which can easily achieve these scan speeds and does not suffer from strong vibrations and ineffective use of the laser capabilities. For this purpose a rotating prism setup may be used in the scanning system 21.

A first possible prism design comprises a rhomboid. Two opposite parallel end faces function as total internal reflection faces (for example having the rhombus shape as shown in FIG. 1 in side view). They are at 45 degrees to the incident light direction. The two internal reflections in the prism provide a lateral shift of an incident beam, so that exit beam is parallel but laterally shifted relative to the input beam. By rotating the prims about an axis perpendicular to the lateral shift direction, and therefore parallel to the incident beam direction a circular path is swept by the output beam. The rotation is about the axis of the input beam. The radius of the circle swept is the length of the rhomboid. Rhomboid prisms can be manufactured with anti-reflection coatings on the faces where required.

A second possible prism design is a dove prism. The two end faces function as refraction interfaces, and the bottom face functions as a total internal reflection face. The end faces are at 45 degrees to the incident light but they are at 90 degrees to each other rather than parallel to each other as for a rhomboid prism (hence with a different side view to that shown schematically in FIG. 1). The two refractions and the single total internal reflection in the prism again provide a lateral shift of an incident beam, so that exit beam is parallel but laterally shifted relative to the input beam. By rotating the prims about an axis perpendicular to the lateral shift direction, and therefore parallel to the incident beam direction, a circular path is swept by the output beam. The rotation is about the axis of the input beam. The amount of beam translation depends on the position of the incident beam relative to the input surface of the dove prism and on the size of the prism. The prism is rotated around the chief incident ray. Anti-reflection coatings may again be added on the angled surfaces to reduce losses by reflection.

The rotating prism is mechanically balanced to avoid vibration. A prism mount is suspended on ball bearings and connects directly to a motor rotor so as to minimize the influence of the aberration correction settings on the effective numerical aperture of the focused light.

In a first aspect, this invention relates in particular to the focusing system 23, and provides a lens system that enables the focal position to be adjusted while also providing optimal coupling to the skin, with or without use of a coupling medium such as transparent sheet applied between skin and system. The design aims to prevent contact window/exit lens damage and skin damage, and thus provides improved safety and increased efficacy of treatment. These objectives are achieved based on the combination of a specially designed and custom made skin contact window/lens and a commercially available aspheric lens.

Figure 3:
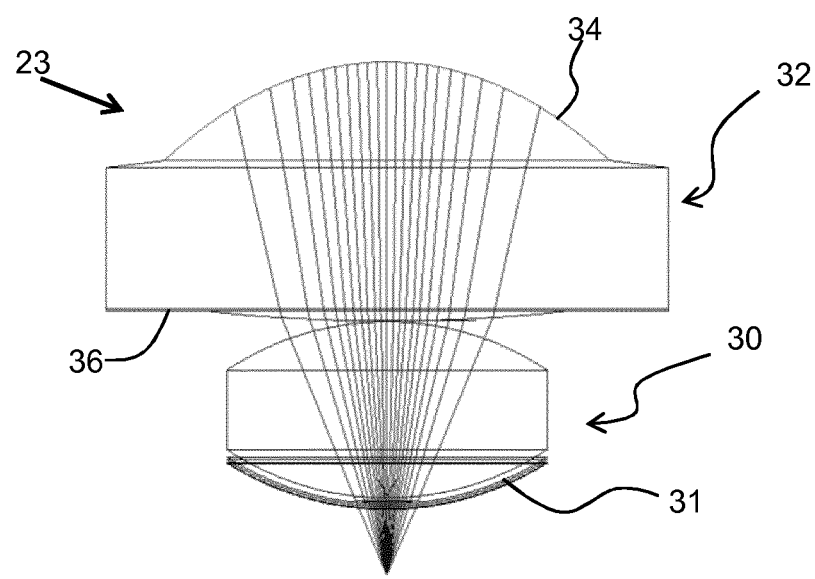
FIG. 3 shows a focusing system design.

FIG. 3 shows a design of the focusing system 23. It comprises the combination of a focusing lens 30 through which the light exits the device before entering the skin and a pre-focusing lens 32.

The lens 30 is manufactured from an optical material such as optical glass, preferably with Abbe number in the range 50 to 85 to minimize dispersion. Most preferably the refractive index of this lens is close to 1.4, i.e. the refractive index of skin. A match as good as possible will reduce reflections between the focusing system exit surface and the skin surface (with or without a transparent sheet applied between), therewith reducing damage caused by reflections of surface of both system and skin. Preferably the refractive index is between 1.4 and 1.6 or between 1.4 and 1.55 or even between 1.4 and 1.5. The optical material is preferably also chosen to withstand the high laser light beam intensities used for the LIOB generation in the skin. Inorganic materials are preferred over plastic materials. Taking account of the above, for example, the Borosilicate Crown (BK) glass and in particular the BK7 type may be used. These have refractive indices of 1.5, which is above but close to 1.4 while providing good material stability and Abbe number for LIOB generation with reduced reflections. Alternatively, fused silica lens may be used which has index of refraction of 1.46. Most preferably the focusing lens is manufactured from BK7 optical glass or Fused Silica.

The lens 30 comprises a bi-convex lens, for example in this case a fused silica bi-convex lens. It has anti-reflection coatings 31 on at least the side of the output surface suitable for the 1064 nm high power laser. The convex surfaces on each side of the lens have the same curvature and design.

The lens 30 has a first, input surface, and a second, output surface. The first surface is spherical and creates a focus to a particular focal point in the skin. The second surface is also spherical and is for direct contact with the skin. The spherical surfaces avoid introducing aberration. The second surface does not damage the focus angles of the rays, particularly as the refractive index is matched to the skin with which the lens makes contact. It preferably has a high damage threshold. The numerical aperture of the lens is increased by a factor corresponding to the refractive index of the skin. The numerical aperture becomes invariant to the depth of focus.

The high numerical aperture of the lens 30 means it is practically not feasible to scan the focus from the scanning system over a very significant part of size of the objective lens. As an example, the typical area that can be scanned by beam deflection over a fixed high numerical aperture objective lens is about 10% of the radius of the lens itself. This would for example be limited to a few hundred micrometers. The higher the numerical aperture, the more difficult it becomes, so that the scan area is limited even further to only a few tens of micrometers, which is within the size of a single treatment zone. Hence, the scanning involves movement of the objective lens as a whole.

The lens 32 comprises a commercially available aspheric lens able to sustain the laser intensity. The purpose of the lens 32 is to convert near collimated light 11 (see FIG. 1) into a desired convergence angle. The lens 32 has a first lens aspheric surface 34 which, with the lens 32 in air only, focuses to the same depth as the focusing lens 30. The lens 32 has a high numerical aperture (in air), such as 0.7 or higher.

The light rays after having passed the first lens surface 34 of the focusing system are shown in FIG. 3.

Suitable aspheric lenses are known for use with laser diodes, photodiodes and fiber coupling systems, and in the field of optical data recording. By way of example, suitable lenses are manufactured by LightPath Technologies Inc.

The lens 32 has a convex first, light input, surface 34 and a planar light exit surface 36 or else a convex light exit surface 36 with a lens surface with greater radius of curvature than the light input surface.

The aspheric lens may be used slightly off its design wavelength, for example of 780 nm, resulting in a slightly lower refractive index of the ECO-550 glass material from which it is manufactured in this case. As a consequence, the convergence of the light incident on the aspheric surface then needs to be corrected for this effect i.e. slightly convergent incidence is required.

The lens 32 may be formed of the same material as the lens 30 but it may be made of a lower cost and easier to manufacture material since the intensity is lower in the lens 32 compared to the other lenses. Thus, the lens 32 may be made of BK7 optical glass or Fused Silica or other materials.

The pre-focusing lens 32 for example comprises a Lightpath 352230-1064 lens with focal distance f=4.55 mm, and NA=0.55 with a 1064 nm antireflection coating.

The lens 30 for example comprises a fused silica bi-convex lens with a 1064 nm antireflection coating, and with lens surfaces radius of curvature $r_{1,2}$=3.2248 mm, a diameter of 3.6 mm and thickness of 2 mm measured in the center of the lens 30 along its optical axis.

The spacing between the two lenses 30, 32 is adjustable to vary the focal depth. This may be manual but preferably is electrically or otherwise apparatus controllable. The adjustment could be carried out during treatment, although it is preferably controlled such as to happen when the laser light is at least not entering the lens 30, but preferably not entering the focusing system. Typically focal depth adjustment is not carried out in real time during treatment.

There is a control path between the controller 25 and the focusing system 23 as shown in FIG. 1. The adjustment is shown in FIG. 4.

Feedback control may be used for example using light received from the skin and an image sensor and image processor. As indicated herein before, such light may be the visible double frequency laser light generated in the skin. The image captured by the image sensor may then be used to determine the nature of the contact between the focusing system and the skin tissue and the focus may be adjusted accordingly. This adjustment may for example take account of the dryness of the skin.

Figures 4A, 4B:
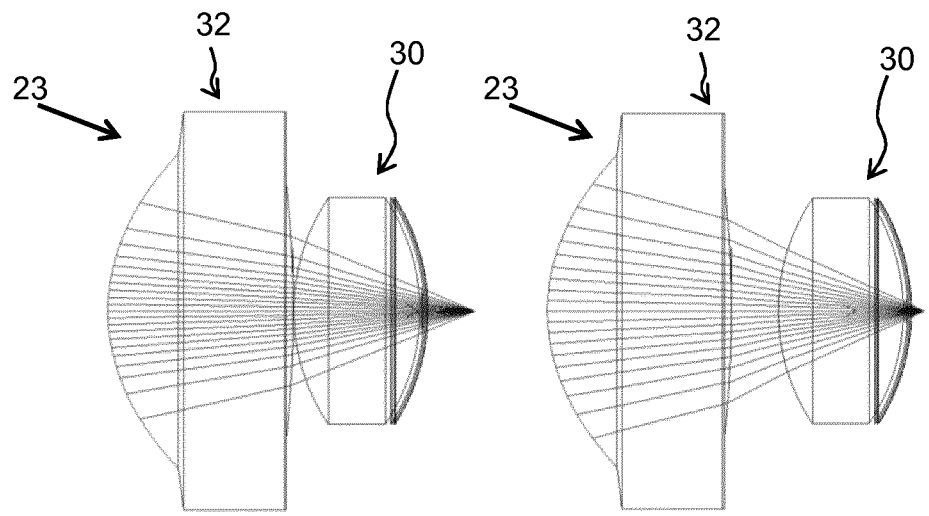
FIG. 4 shows the focusing system design of FIG. 3 at the two extreme focus positions.

FIG. 4A shows a first zero spacing between the two lenses, which corresponds to a maximum focal depth of for example around 750 μm. FIG. 4B shows a maximum spacing between the two lenses, which corresponds to a minimum focal depth for example of around 200 μm. To a first order, the depth of the focus relative to the lens 32 remains constant.

The combination of the two lenses introduces some limitations with respect to the user specification. This is related to the limited free working distance of the aspheric lens 32, combined with the limitations on the minimum achievable thickness of the skin contact lens 30. As a consequence, the maximum achievable treatment depth inside the dermis may be approximately 750 um, slightly less than a preferred 1 mm.

The relative shift in distance between the two lenses implies that some aberration correction means need to be installed to compensate. Examples of how to implement this aberration correction are discussed below.

Additionally, the aspheric lens in the example above is used slightly off its design wavelength of 780 nm, resulting in a slightly lower refractive index of the ECO-550 glass material from which it is manufactured. As a consequence, the convergence of the light incident on the aspheric surface needs to be corrected for this effect, i.e. slightly convergent incidence is required.

The invention relates to LIOB based skin treatment devices. The focusing system gives improved contact with the skin, uniform optical coupling, and it prevents contact window/exit lens damage and skin damage. It also allows seamless contour following for skin treatment or even shaving if desired. Thus, the skin treatment may comprise a hair removal shaving process. During use, the focusing system 23 is moved over the skin surface to be treated or shaved. The focusing system forms an exit window for allowing the incident light beam to leave the device. The focusing system then forms an optical blade The skin treatment may comprise skin rejuvenation device for reducing wrinkles that may appear in human skin as a result of normal aging processes. During use, the focusing element is pressed onto or kept close to the skin to be treated. The exit window formed by the focusing system is held parallel to the skin and the incident light beam leaves the exit window and enters the skin in a direction substantially perpendicular to the skin surface. As described in WO2013/128380 a transparent sheet including one or more index matching fluids may be provided between the focusing lens (or, if present an exit window of a further flat exit window) and the skin. This is a preferred setup and way of use of the current invention as it may enhance lateral movement of the focusing system over the skin, or rather the top surface of the transparent sheet. The sheet can be used for improved index matching as well as skin flattening by pulling the skin against it through capillary forces of the roughness of stratum cornea as also described in detail in WO2013/128380. Details of such sheet or foil are disclosed in the reference provided and are intended to be part of this invention, but for sake of brevity will need not be repeated here.

Thus in all application of a device according to the invention, an immersion fluid may be provided between the focusing system and the skin surface. Preferably, an immersion fluid is used with a refractive index close to the refractive index of the skin contact lens of the focusing system 23 and the skin or hair where the LIOB is to occur. For this purpose, fluids with a refractive index of about 1.4 to about 1.5 are suitable. Also water, although having a somewhat lower refractive index of 1.33, may for some devices and applications be a suitable immersion fluid. Fluid examples suitable for use with transparent sheet are provided in WO2013/128380.

As mentioned above, the variable focus capability means that some aberration correction may need to be installed to compensate.

This aberration correction may be implemented at various points in the system, for example before or after beam shaping (by beam shaping system 19). Furthermore, the beam shaping system 19 may be implemented by the focusing system 23 so that only aberration correction is provided between the beam reflecting system 17 and the scanning system 21.

To correct for the spherical aberration that is expected when focusing at different depths inside the skin, the divergence of the beam incident on the scanning prisms of the scanning system 21 may be made adjustable.

A simplest solution would be to allow the user to adjust the divergence of the beam by manipulating one or more lens positions. However, since the placement of these lenses is quite critical and the system needs to be operable by users without a background in laser optics, it would be better to implement some form of automated correction that adjusts the position or strength of a lens depending on the selected focusing depth, or even on the fly, for example depending on the observed LIOB flash intensity.

A second aspect of the invention relates to aberration correction.

Since motorized focusing typically consumes a lot of space and is mechanically complex and typically too slow to accommodate for dynamic variations, an adaptive optical element is preferred.

Two examples of suitable adaptive optical element are an electrically tunable low dispersion polymer lens, and a liquid focusing lens. These are two examples of electrically tunable lenses.

An electrically tunable low dispersion polymer lens is based on the elastic deformation of a flexible polymer by means of a voice coil actuator. Such lenses are for example commercially available from the company Optotune (trade mark). A liquid focusing lens is based on the principle of electrowetting, whereby the curvature of the contact surface between a low refractive index water phase and high refractive index oil phase liquid is varied by changing the wetting properties of the surfaces of the lens mount. Such lenses are for example commercially available from the company Varioptic (trade mark) or Optilux (trade mark). Such lenses have also been described in e.g. U.S. Pat. Nos. 7,616,737 or 7,808,717 and references therein.

The low dispersion polymer lens has benefits in terms of a large aperture diameter for example of 10 mm compared to a 2.5 mm diameter of off-the-shelf liquid focusing lenses. A larger lens makes alignment less challenging. A disadvantage of the polymer lens is related to its sensitivity to temperature, which could lead to wrong focusing depths and/or physical damage when running either at continuous high laser power or high electrical drive currents to the voice coil. The fluid focusing lens has the advantage of drawing very little current.

The lenses are preferably provided with coatings that are suitable for 1064 nm high power laser light.

Figure 5:
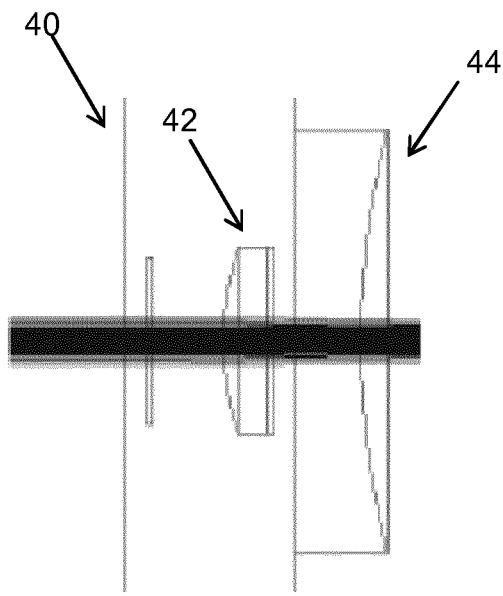
FIG. 5 shows a first example of a lens system for providing aberration compensation.

FIG. 5 shows a variable lens design based on a polymer lens.

FIG. 5 shows a control unit 40 (voice coil), the polymer lens 42 and an additional negative lens 44.

The negative lens compensates for the overall positive polymer lens focal length, such that the light will still be still almost collimated after passing through the two lenses. The additional negative lens 44 is used to allow the beam to be adjustable in a suitable range between convergent and slightly divergent.

The polymer lens comprises a housing which holds the voice coil and associated mechanics, and a number of windows to protect the sensitive convex polymer surface from external influences.

The purpose of the adjustment is to compensate for aberrations induced by the complete optical system. The focusing system actually comprises a number of lenses and the skin itself. This system may vary due to a number of causes:

(i) The user or operator selecting a different set of focusing lenses to change the treatment depth inside the skin.
(ii) The incident laser beam undergoing changes due to e.g. changes in operating temperature.
(iii) Change of the refractive index profile in the skin being treated owing to different hydration levels etc.

The adjustment may slightly vary the divergence of the beam incident on the objective lenses (while keeping the diameter of the beam mostly unaffected), which can be used to reduce the influence of the effects mentioned above on the focusing quality. Furthermore, optical simulation has shown that by using these kinds of tools also higher order aberrations can be effectively reduced (in particular 3rd order spherical aberrations).

The variable lens design is placed before the aspheric lens 32 of the focusing system 23.

In order to limit the impact of the variable divergence on the diameter of the beam incident on the aspheric lens 32 of the focusing system 23, the aberration correction elements are placed as close as possible to the scanning system 21, effectively limiting the amount of space that is available for placement of mechanical components and scanning motors.

Figure 6:
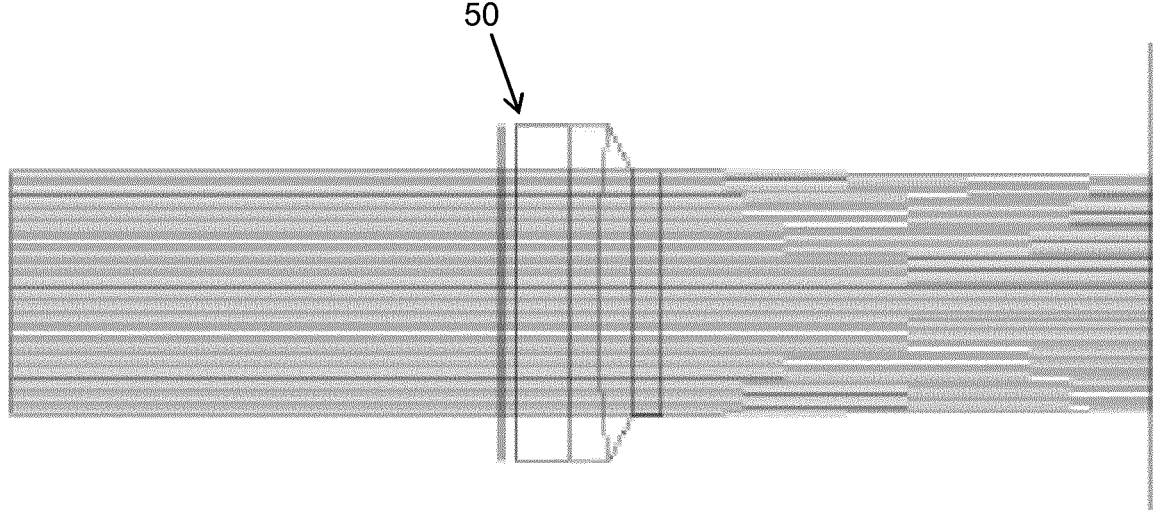
FIG. 6 shows a second example of a lens system for providing aberration compensation.

FIG. 6 shows a ray trace of the electrowetting lens 50 used for aberration correction.

The lens introduces a very small amount of convergence. No additional compensation for initial curvature is required for this lens. The lens may instead be required to introduce a small amount of divergence. The incident beam is close to collimated and the required correction is typically small.

Figure 7:
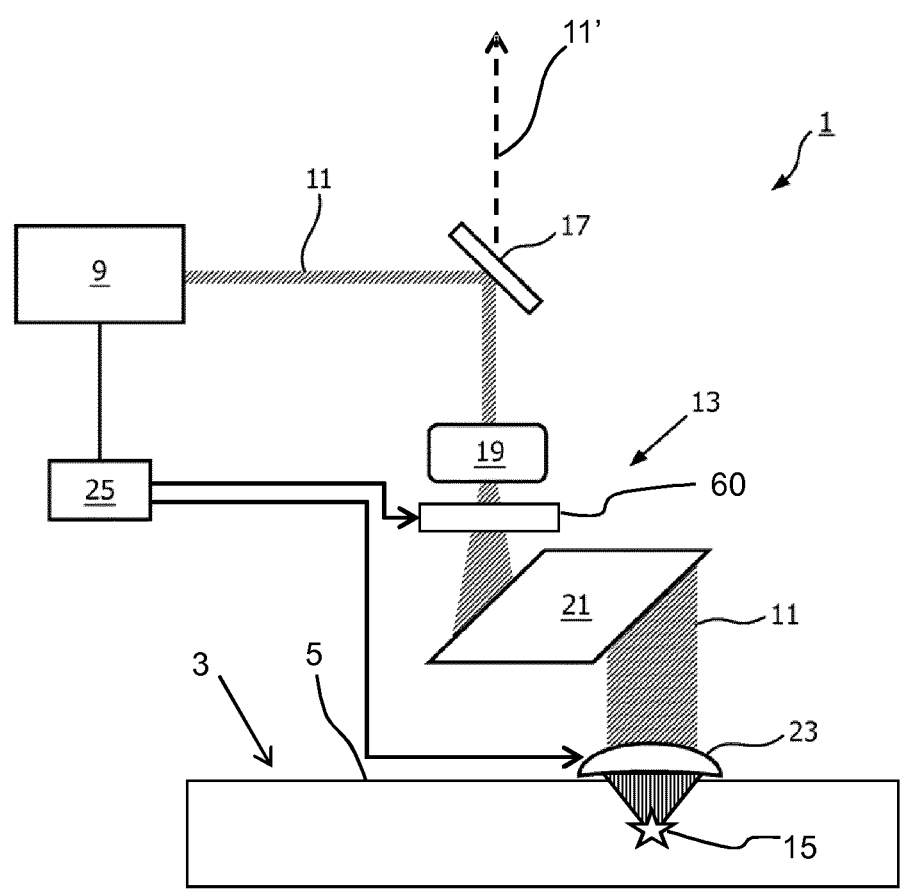
FIG. 7 shows the system of FIG. 1 modified to include the lens system for aberration compensation.

FIG. 7 shows the system of FIG. 1 modified to include the adjustable lens system 60 for aberration correction of the focusing system 23. The adjustable lens system 60 is controlled by the controller 25 in synchronism with the adjustment of the focus depth setting of the focusing system 23, so that aberration correction is matched to the setting of the focusing system 23. The adjustable lens system 60 is provided at the input to the scanning system 21.

The scanning system for example comprises a set of of objective lenses 23 for different depths. The adjustable lens system is shared by each of these objective lenses, whereas the chosen objective lens is scanned over the skin. Thus, the aberration correction component remains in the static part of the system. The aberration correction takes account of the focus depth, i.e. the objective lens which is chosen, as well as the aberration introduced by all other components in the optical path. The aim is to compensate for spherical aberration without changing the beam diameter. The spherical aberration is for example introduced by the pre-focusing lens 32.

Thus, the aberration correction system, which may be bulky and heavy does not need to be scanned with the focusing system 23 (objective lenses), which would make scanning at high speeds and in continuous motion difficult because of the need of gliding electrical contacts etc. and because the motion could also induce vibration to the tunable lenses themselves. The focusing lenses and mounts forming the focusing system 23 weigh only a few grams. The polymer tunable lens for example weighs only tens of grams excluding the associated mounts and plano-concave lenses.

Thus, the aberration correction is static in space, although it may be varied in time depending on various feedback means which are spatially dependent (e.g. based on flash intensity or audible feedback).

The system of FIGS. 1 and 7 have one particular set of optical components between the laser and the focusing system. However, this arrangement is not intended to be limiting. The focusing system and the aberration compensation system of the invention may be used in different system configurations with a smaller or greater number of components. As is clear from the description above, the invention relates specifically to the final focusing system which makes contact with the skin and to the aberration compensation system.

The aberration correction is of particular interest for an electrically adjustable focusing system such as described in connection with the first aspect of the invention. However, the aberration correction may also be used in connection with a mechanically adjustable focusing system such as shown in FIG. 2.

In particular, not all aberrations can be controlled in a selectable set of adjustments, so fine tuning may be desired on a case by case basis or in a dynamic manner.

The aberration correction system does not have sufficient power to affect the focusing depth significantly, so that an indexing system (of FIG. 2) may be combined with the aberration correction system.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A light based skin treatment device, comprising:
   a light source for providing a pulsed incident light beam for generating laser induced optical breakdown of hair or skin tissue;
   an adjustable focusing system for focusing the pulsed incident light beam into a focal spot in the hair or skin tissue;
   a scanning system for scanning the focal spot; and
   an electrically adjustable lens system arranged in an optical path before the adjustable focusing system for providing compensation for aberration, wherein the electrically adjustable lens system is provided at an input to the scanning system.

2. The light based skin treatment device according to claim 1, wherein the electrically adjustable lens system comprises a tunable lens adapted to change a focal distance.

3. The light based skin treatment device according to claim 2, wherein the electrically adjustable lens system further comprises a negative lens arranged in the optical path behind the tunable lens.

4. The light based skin treatment device according to claim 2, wherein the tunable lens is electrically tunable.

5. The light based skin treatment device according to claim 4, wherein the tunable lens comprises an electrically tunable polymer lens or a fluid focus lens.

6. The light based skin treatment device according to claim 1, wherein the adjustable focusing system comprises:
   a pre-focusing lens for increasing a convergence of the pulsed incident light beam;
   a focusing lens having convex light input and light exit surfaces; and
   a focus controller for controlling a distance from the adjustable focusing system to the focal spot by adjusting a spacing between the pre-focusing lens and the focusing lens.

7. The light based skin treatment device according to claim 6, wherein the pre-focusing lens comprises an aspheric lens.

8. The light based skin treatment device according to claim 6, wherein the pre-focusing lens comprises:
   a convex light input surface; and
   a planar light output surface or a convex light output surface with an average radius of curvature greater than the average radius of curvature of the convex light input surface.

9. The light based skin treatment device according to claim 6, wherein the focusing lens is formed of Borosilicate Crown (BK) glass or fused silica.

10. The light based skin treatment device according to claim 6, wherein the focusing lens is configured for contacting skin and comprises an anti-reflection coating.

11. A method for providing a light based skin treatment, comprising:
    providing a pulsed incident light beam for generating laser induced optical breakdown of hair or skin tissue;
    focusing the pulsed incident light beam into a focal spot in the hair or skin tissue using an adjustable focusing system;
    scanning the focal spot across the hair or skin tissue using a scanning system; and
    providing compensation for aberration in the adjustable focusing system using an adjustable lens system arranged in a light path before the adjustable focusing system at an input to the scanning system.

12. The method according to claim 11, further comprising using an electrically tunable polymer lens or an electrowetting lens to provide the compensation for aberration.

13. The method according to claim 11, wherein providing compensation for aberration comprises:
- using a pre-focusing lens for increasing a convergence of the pulsed incident light beam;
- focusing onto the hair or skin tissue using a skin contact lens having convex light input and light exit surfaces; and
- controlling a distance from the adjustable focusing system to the focal spot by adjusting a spacing between the pre-focusing lens and the skin contact lens.

14. A light based skin treatment system, comprising:
- a light source for providing a pulsed incident light beam for generating laser induced optical breakdown of hair or skin tissue;
- an adjustable focusing system for focusing the pulsed incident light beam into a focal spot in the hair or skin tissue;
- a scanning system for scanning the focal spot;
- an electrically adjustable lens system disposed at an input to the scanning system, and arranged in an optical path before the adjustable focusing system;
- a controller; and
- a non-transitory computer readable medium that stores instructions, which when executed by the controller causes the electrically adjustable lens system to provide compensation for aberration.

15. The light based skin treatment system according to claim 14, wherein the electrically adjustable lens system comprises a tunable lens adapted to change a focal distance.

16. The light based skin treatment device according to claim 15, wherein the electrically adjustable lens system further comprises a negative lens arranged in the optical path behind the tunable lens.

17. The light based skin treatment device according to claim 15, wherein the tunable lens is electrically tunable.

18. The light based skin treatment device according to claim 17, wherein the tunable lens comprises an electrically tunable polymer lens or a fluid focus lens.

19. The light based skin treatment system according to claim 15, wherein the adjustable focusing system comprises:
- a pre-focusing lens for increasing a convergence of the pulsed incident light beam;
- a focusing lens having convex light input and light exit surfaces; and
- a focus controller for controlling a distance from the adjustable focusing system to the focal spot by adjusting a spacing between the pre-focusing lens and the focusing lens.

20. The light based skin treatment system according to claim 19, wherein the pre-focusing lens comprises:
- a convex light input surface; and
- a planar light output surface or a convex light output surface with an average radius of curvature greater than the average radius of curvature of the convex light input surface.

* * * * *